US011871999B2

(12) United States Patent
Krimsky et al.

(10) Patent No.: US 11,871,999 B2
(45) Date of Patent: Jan. 16, 2024

(54) SYSTEM, APPARATUS, AND METHOD FOR NAVIGATING TO A MEDICAL TARGET

(71) Applicant: Covidien LP, Mansfield, MA (US)

(72) Inventors: William S. Krimsky, Forest Hill, MD (US); Michael J. Kern, Minnetonka, MN (US); Lev A. Koyrakh, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 285 days.

(21) Appl. No.: 17/492,837

(22) Filed: Oct. 4, 2021

(65) Prior Publication Data

US 2022/0015837 A1 Jan. 20, 2022

Related U.S. Application Data

(63) Continuation of application No. 15/905,947, filed on Feb. 27, 2018, now Pat. No. 11,154,365.

(60) Provisional application No. 62/468,482, filed on Mar. 8, 2017.

(51) Int. Cl.
| *A61B 5/00* | (2006.01) |
| *A61B 34/20* | (2016.01) |
| *A61B 1/267* | (2006.01) |
| *A61B 5/0515* | (2021.01) |
| *A61B 5/06* | (2006.01) |
| *G06T 17/00* | (2006.01) |

(Continued)

(52) U.S. Cl.
CPC ........ *A61B 34/20* (2016.02); *A61B 1/000094* (2022.02); *A61B 1/2676* (2013.01); *A61B 5/0515* (2013.01); *A61B 5/062* (2013.01); *A61B 5/065* (2013.01); *G06T 17/00* (2013.01); *G06T 19/003* (2013.01); *A61B 2034/2051* (2016.02); *A61B 2034/2065* (2016.02)

(58) Field of Classification Search
CPC .............. A61B 1/00009; A61B 1/2676; A61B 2034/2051; A61B 2034/2065; A61B 34/20; A61B 5/0515; A61B 5/062; A61B 5/065; G06T 17/00; G06T 19/003
See application file for complete search history.

(56) References Cited

U.S. PATENT DOCUMENTS

| 6,272,370 B1 | 8/2001 | Gillies et al. |
| 7,775,972 B2 | 8/2010 | Brock et al. |
| 8,241,274 B2 | 8/2012 | Keogh et al. |

(Continued)

FOREIGN PATENT DOCUMENTS

EP 3146929 A1 3/2017

OTHER PUBLICATIONS

Extended European Search Report for Application No. 18160455.4, dated Jul. 11, 2018.

*Primary Examiner* — Mark D Remaly
(74) *Attorney, Agent, or Firm* — Carter, DeLuca & Farrell LLP

(57) ABSTRACT

A system for monitoring an approach to a target includes a luminal device including a distal portion, a sensor coupled to the distal portion of the luminal device, and a surgical instrument including one or more indicators having a detectable property located along at least a portion of the surgical instrument. The luminal device is configured to be inserted into a patient, and the distal portion of the luminal device is configured to be guided proximate a target. The sensor is configured to sense the detectable property of the one or more indicators. The surgical instrument is configured to be guided through the luminal device.

20 Claims, 7 Drawing Sheets

(51) Int. Cl.
*G06T 19/00* (2011.01)
*A61B 1/00* (2006.01)

(56) References Cited

U.S. PATENT DOCUMENTS

| | | |
|---|---|---|
| 11,154,365 B2 | 10/2021 | Krimsky et al. |
| 2003/0078494 A1 | 4/2003 | Panescu |
| 2013/0223702 A1 | 8/2013 | Holsing et al. |
| 2014/0046174 A1 | 2/2014 | Ladtkow et al. |

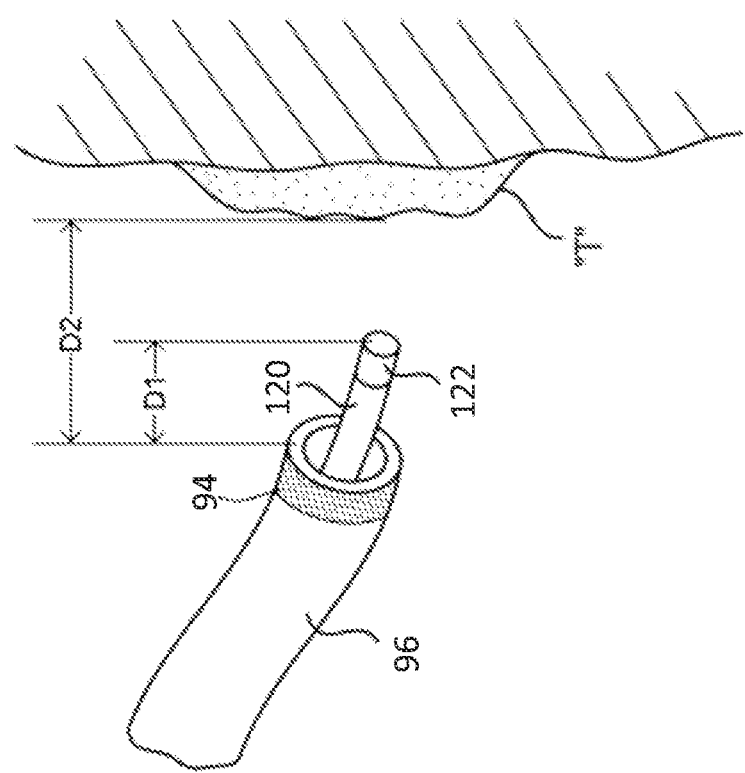

SYSTEM, APPARATUS, AND METHOD FOR NAVIGATING TO A MEDICAL TARGET

CROSS REFERENCE TO RELATED APPLICATIONS

The present application is a continuation application of U.S. patent application Ser. No. 15/905,947, filed on Feb. 27, 2018, which claims the benefit of and priority to U.S. Provisional Application Ser. No. 62/468,482, filed on Mar. 8, 2017, the entire contents of each of which being incorporated herein by reference.

FIELD

The present disclosure relates generally to systems and methods for navigating a tool, such as a catheter, probe, or medical device, through a luminal network of a patient's body to a target site and tracking the location of the tool as it approaches the target site. Specifically, the present disclosure relates to a navigation system and a method for determining and displaying the distance between a tool and a target site.

BACKGROUND

A common device for inspecting the airway of a patient is a bronchoscope. Typically, the bronchoscope is inserted into a patient's airways through the patient's nose or mouth and can be extended into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments, can be inserted.

Bronchoscopes, however, are limited in how far they may be advanced through the airways due to their size. Where the bronchoscope is too large to reach a target location deep in the lungs, a clinician may utilize certain real-time imaging modalities such as fluoroscopy. Fluoroscopic images, while useful, present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™), system currently sold by Medtronic plc. The details of such a system are described in commonly assigned U.S. Pat. No. 7,233,820, entitled ENDOSCOPE STRUCTURES AND TECHNIQUES FOR NAVIGATING TO A TARGET IN BRANCHED STRUCTURE, filed on Mar. 29, 2004, by Gilboa, and commonly assigned U.S. Pat. No. 9,247,992, entitled SYSTEM AND METHOD FOR NAVIGATING WITHIN THE LUNG, by Brown, the entire contents of which are incorporated herein by reference.

While the system as described in U.S. Pat. No. 7,233,820 is quite capable, there is always a need for development of improvements and additions to such systems.

SUMMARY

Provided in accordance with the present disclosure is a system for monitoring an approach to a target. The system includes a luminal device having a distal portion, a sensor coupled to the luminal device, and a surgical instrument. The luminal device is configured to be inserted into a patient and the distal portion of the luminal device is configured to be guided proximate a target. The surgical instrument includes one or more indicators having a detectable property located along at least a portion of the surgical instrument and is configured to be guided through the luminal device. The sensor is configured to sense the detectable property of the one or more indicators.

In an aspect of the present disclosure, the system further includes an electromagnetic field generator, a display, and a computing device including a processor and a memory storing instructions. The electromagnetic field generator is configured to detect a location of the sensor as it is navigated within the patient. The display is capable of displaying an image of the sensor within the patient. The computing device, when the memory storing instructions are executed by the processor, generates a model of a region of interest containing the target based on images of the region of interest, identifies the target within the model of the region of interest, and tracks the location of the sensor while the sensor is navigated within of a region of interest.

In another aspect of the present disclosure, the region of interest is a luminal network.

In an additional aspect of the present disclosure, the detectable property is ferromagnetism.

In yet another aspect of the present disclosure, the system further includes an electromagnetic field generator configured to detect the sensor. The sensor is an electromagnetic sensor capable of detecting a change in the electromagnetic field caused by the one or more indicators.

In another aspect of the present disclosure, the one or more indicators are stripes or flecks.

In an additional aspect of the present disclosure, the luminal device is one of a catheter, a needle, or a trocar.

In yet another an aspect of the present disclosure, the one or more indicators are painted on the surgical instrument or the indicators are implanted within the surgical instrument In another aspect of the present disclosure, the one or more indicators are located at even intervals along a length of the surgical instrument.

In an additional aspect of the present disclosure, the one or more indicators include a plurality of indicators each having a distinct known material composition or concentration of charged particles that defines each of the one or more indicators or defines a progression of the one or more indicators.

In yet another aspect of the present disclosure, the system further includes a second sensor coupled to the luminal device at a different location than a location of the sensor and configured sense the detectable property of the one or more indicators.

Provided in accordance with the present disclosure is a method for monitoring an approach to a target. The method includes identifying a location of a target site within a patient's body, navigating or placing the distal portion of the luminal device proximate a target, navigating or placing a surgical instrument through the luminal device proximate the target, advancing a distal portion of the surgical instrument beyond the distal portion of the luminal device, and determining a distance that the distal portion of the surgical instrument has advanced beyond the luminal device.

In an aspect of the present disclosure, the method further includes determining a distance between the distal portion of the surgical instrument and the location of the target.

In an another aspect of the present disclosure, determining a distance that the surgical instrument has advanced beyond the luminal device includes sensing indicators on the surgical instrument as the indicators are advanced past a sensor coupled to the luminal device and determining, according to known distances between the indicators on the surgical instrument and a location of the sensor, a distance between the distal portion of the surgical instrument and the distal portion of the luminal device as well as between the end of the surgical instrument and the target.

In an additional aspect of the present disclosure, the indicators are one of stripes or flecks.

In yet another aspect of the present disclosure, the method further includes generating an electromagnetic field about the patient, the sensor includes magnetic field sensors configured to sense the magnetic field, and sensing the indicators includes sensing a change in the magnetic field caused by the indicators.

In another aspect of the present disclosure, the method further includes generating a model of a luminal network based on images of the luminal network, and navigating the distal portion of the luminal device proximate the target includes navigating the distal portion of the luminal device through the luminal network.

In an additional aspect of the present disclosure, the method further includes tracking a location of a location sensor coupled to the distal portion of the luminal device while the location sensor is navigated within the luminal network, and displaying guidance for navigating the location sensor within the luminal network.

In yet another aspect of the present disclosure, the method further includes generating an electromagnetic field about the luminal network and inserting the location sensor into the electromagnetic field. The location sensor includes magnetic field sensors configured to sense the magnetic field and to generate position signals in response to the sensed magnetic field.

BRIEF DESCRIPTION OF THE DRAWINGS

Various embodiments of the present disclosure are described herein with reference to the drawings wherein:

FIG. 5 is a perspective partial-view of a distal portion of an embodiment of a catheter and a tool in a surgical site, in accordance with the present disclosure;

DETAILED DESCRIPTION

Figure 1:
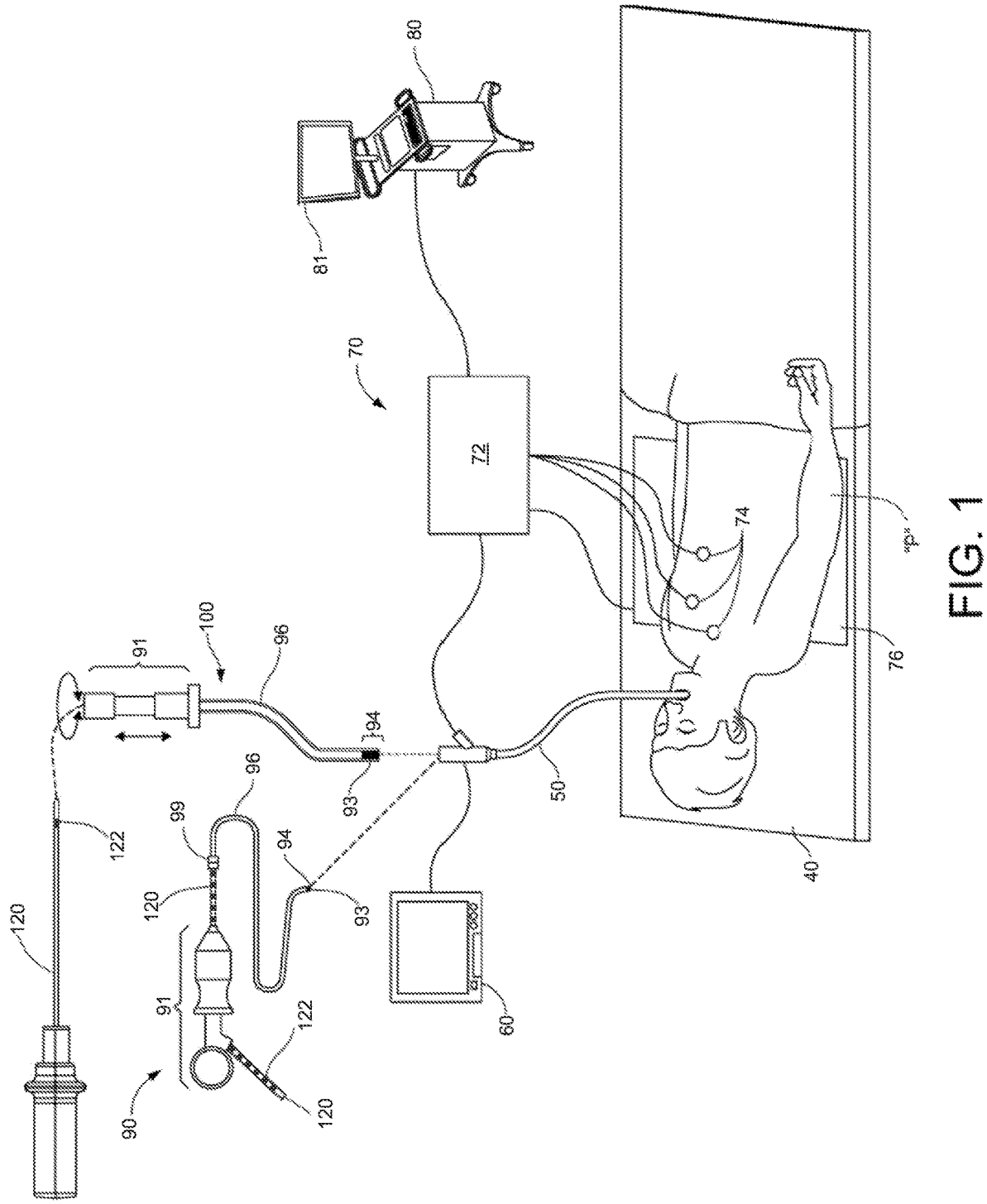
FIG. 1 is a schematic illustration of an electromagnetic navigation (EMN) system and two catheter guide assemblies configured to be used with the EMN system, in accordance with an embodiment of the present disclosure.

The present disclosure is directed to a navigation or location tracking system and a method for determining and displaying the distance between a tool and a target site. Generally, an indicator possessing a detectable property is included on a tool to thereby permit a sensor disposed within a patient and coupled to a guiding device to sense the presence or proximity of the tool. The ability to locate an indicator coupled to a tool allows for a precise locating of the tool without introducing an additional sensor into the system which would cause additional expense, reduce flexibility of the tool, and require re-registration when the tool is used in a new system.

Embodiments of the presently disclosed navigation or location tracking systems are now described in detail with reference to the drawings, in which like reference numerals designate identical or corresponding elements in each of the several views. As used herein the term "distal" refers to that portion of the navigation system, or component thereof, farther from a user (e.g., clinician), while the term "proximal" refers to that portion of the navigation system, or component thereof, closer to the user.

Detailed embodiments of the present disclosure are described herein; however, the described embodiments are merely examples of the disclosure, which may be embodied in various forms. Therefore, specific structural and functional details described herein are not to be interpreted as limiting, but merely as a basis for the claims and as a representative basis for teaching one skilled in the art to variously employ the present disclosure in virtually any appropriately detailed structure.

FIG. 1 shows an electromagnetic navigation (EMN) system 70 configured for use with a catheter guide assembly 90, 100, in accordance with an illustrative embodiment of the present disclosure. The EMN system 70 is configured to utilize computerized tomography (CT) imaging, magnetic resonance imaging (MRI), ultrasonic imaging, endoscopic imaging, fluoroscopic imaging, or another modality to create a roadmap of a patient's lungs. One such EMN system 70 is the ELECTROMAGNETIC NAVIGATION BRONCHOSCOPY® system currently sold by Medtronic plc. The EMN system 70 generally includes a bronchoscope 50 configured to receive one or more types of catheter guide assemblies 90, 100, monitoring equipment 60, an electromagnetic field generator 76, a tracking module 72, and a workstation 80, which includes application 81, a software application for operating the workstation system. FIG. 1 also depicts a patient "P" lying on an operating table 40 including electromagnetic field generator 76. The positions of a number of reference sensors 74 placed on the patient "P" in the magnetic field generated by the electromagnetic field generator 76 can be determined by the tracking module 72. The EMN system 70 uses the reference sensors 74 to calculate a patient coordinate frame of reference.

Each of the catheter guide assemblies 90, 100 includes a control handle 91 and an extended working channel (EWC) 96 that is configured to receive a tool 120. The EWC 96 includes an electromagnetic (EM) sensor 94 located on a distal end 93 of the EWC 96 and a locking mechanism 99.

Once inserted in EWC 96, tool 120 can be locked to EWC 96 with locking mechanism 99. Tool 120 may be any one of a variety of medical devices including, but not limited to, a needle, a guide wire, a biopsy tool, a dilator, or an ablation device. In an embodiment, tool 120 also includes an EM sensor 94 and can be used independent of EWC 96. The EM sensor 94 works in conjunction with the tracking module 72 to enable tracking and navigation of the EM sensor 94 within the magnetic field generated by the electromagnetic field generator 76. In particular, the tracking module 72 enables navigation and tracking of the EM sensor 94, including receiving orientation data corresponding to the EM sensors 94, within a luminal network of a patient "P" to arrive at a target site. EM sensor 94 may be any number of types of location sensors, including ring sensors, optical sensors, radiofrequency sensors, ferromagnetic sensors, hollow sensors, and the like.

Alternative systems configured for use with a catheter guide assembly 90, 100, in place of EMN system 70, are also contemplated by the present disclosure. For example, a sonar system or an acoustic system may replace electromagnetic field generator 76 in the illustrative embodiment described in FIG. 1. The sonar or acoustic system generates sound waves that penetrate, reflect from, or are absorbed by various objects according to the material properties and locations of those objects and the frequency of the sound waves created by the sonar or acoustic system. The time at which reflected sound waves are received at the sonar or acoustic system and the frequency of those reflected waves allow tracking module 72 to determine object locations. Specifically, EM sensors 94, or another sensor as the case may be, reflects sound waves at a particular time and frequency according to its location and material properties. Thus, if the reflection signal of the sensor is known, tracking module 72 may determine its position.

Tool 120 further includes indicators 122. As shown in FIG. 1, tool 120 may include a single indicator 122 or multiple indicators 122. Indicators 122 are configured to be sensed by EM sensor 94. In one embodiment, in order to be sensed by EM sensor 94, indicators 122 possess ferromagnetic properties that may be detected by EM sensor 94. Once catheter guide assembly 90, 100 is navigated to and locked in place proximate a target, tool 120 may be advanced through catheter guide assembly 90, 100. Catheter guide assembly 90, 100 may be locked in place by wedging catheter guide assembly 90, 100 into, for example, a luminal passage, by expanding a catheter balloon (not shown), by positioning and engaging an endobronchial valve, or through several additional means commonly known in the art. As tool 120 advances, indicators 122 pass EM sensor 94 which, due to the coupling of EM sensor 122 to catheter guide assembly 90, 100, remains locked relative to the area within the body in with catheter guide assembly 90, 100 is locked. While in a locked position, EM sensor 94 measures minimal changes in the electromagnetic field generated by electromagnetic field generator 76. Therefore, as indicators 122, which possess ferromagnetic properties, pass EM sensor 94, EM sensor 94 senses a change in the electromagnetic field generated by electromagnetic field generator 76. The stability of EM sensor 94 and the change in the electromagnetic field generated by electromagnetic field generator 76 indicate to application 81 that indicator 122 is in proximity of EM sensor 94. As will be appreciated, the greater the proximity of the indicator 122 and the EM sensor 94, the greater the distortion in the electromagnetic field. The magnitude of distortion can be converted to a distance from the EM sensor, which permits the location of the indicator 122 to be calculated. Knowing the location of indicators 122 along the tool allows for the position of the tool within catheter guide assembly 90, 100 to be known. The known location may further be used to update, or provide for the first time, a location of tool 120 within a three-dimensional model of the patient's airways, luminal networks, or other areas of interest.

As noted above, tool 120 may include multiple indicators 122. Multiple indicators 122 allow application 81 to progressively determine a relative position of tool 120 compared to EM sensor 94. In embodiments, indicators 122 are spaced apart a known distance, and application 81 may count indicators 122 to track the movement of tool 120 as it advances toward the target by counting the number of indicators 122 that have been registered by EM sensor 122. In other embodiments, indicators 122 may be spaced unequally along tool 120. Locations of indicators 122 may be saved in memory 702 and read by application 81 in order to determine which indicator 122 has passed EM sensor 94. Alternatively, indicators 122 may possess varying ferromagnetic strength. The ferromagnetic strength of the various indicators 122 may be detected by EM sensor 94 and analyzed, by application 81, to determine an identity and location of an indicator 122 as it passes EM sensor 94. In order to achieve varying ferromagnetic strengths for indicators 122, each indicator 122 may be composed of a different material, a different composition of materials, or a different concentration of doping or charged particles. Varying materials causes each indicator 122 to affect the electromagnetic field with its own unique ferromagnetic strength that may be registered by EM sensor 94 and interpreted by application 81.

EM sensor 94 and indicators 122 which may be detected by EM sensor 94 are described herein. However, the current disclosure contemplates the use of other sensors configured to be used in place of EM sensor 94 and indicators 122 that possess alternative or additional properties which may be measured by EM sensor 94 or other sensors that may be used in place of EM sensor 94. Alternative properties of indicators 122 may be varied in order to be detected and discriminated indicators 122 by sensors other than EM sensor 94. Indicators 122 may, for example, include indicators 122 of various colors. Sensors that may be utilized in place of EM sensor 94 include other electric field sensors, such as Hall Effect sensors, cameras, including visible light, infrared, and ultraviolet cameras, ultrasonic sensors, laser sensors, capacitive sensors, and chemical detection sensors.

EM sensor 94 or any other potential sensor may be a hollow sensor that allows indicators 122 to pass through or EM sensor 94 may have other geometric configurations that allow for coupling to the distal end 93 of the EWC 96. Indicators 122 may possess detectable properties including color, physical dimensions, including thickness, length, and surface roughness, magnetic properties, and capacitive properties, and may output communication signals such as, but not limited to, BLUETOOTH® signals, light signals, sound signals and radiofrequency signals. Indicators 122 are depicted in FIG. 1 as one or more stripes. However, indicators 122 may take on any shape including, but not limited to, stripes, dots, flecks, rings, dashes, triangles, etc.

Figure 2:
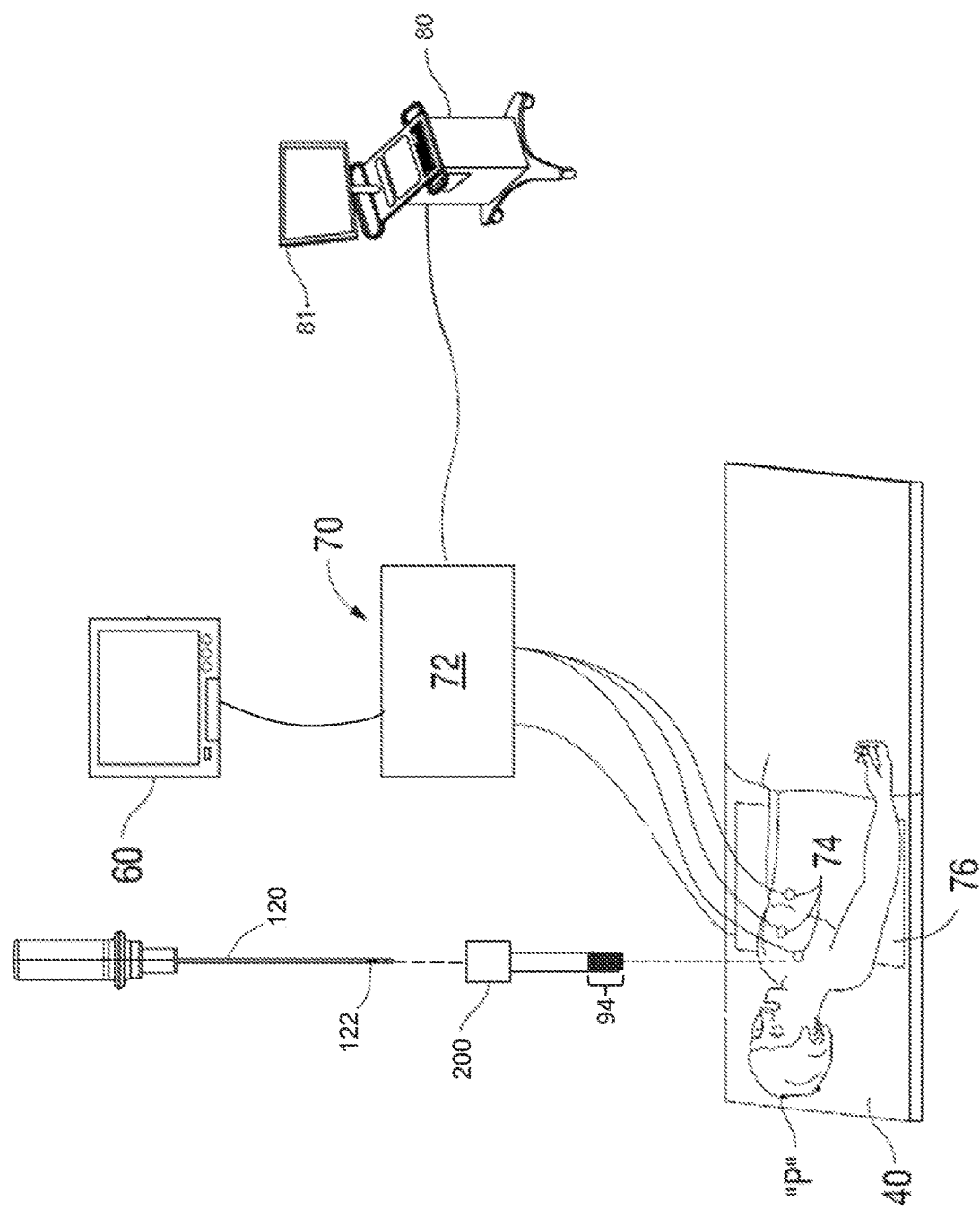
FIG. 2 is a schematic illustration of an electromagnetic navigation (EMN) system and a percutaneous assembly configured to be used with the EMN system, in accordance with an embodiment of the present disclosure.

Now referring to FIG. 2, there is shown an electromagnetic navigation (EMN) system 70 configured for use with an access instrument 200, in accordance with an illustrative embodiment of the present disclosure. In FIG. 2, as with FIG. 1, the EMN system 70 generally includes monitoring equipment 60, an electromagnetic field generator 76, a tracking module 72, and a workstation 80, which includes application 81, a software application for operating the workstation system, operating table 40 including electromagnetic field generator 76, and reference sensors 74 placed on the patient "P" in the magnetic field. In FIG. 2, EMN system 70 operates in a similar manner as described with respect to FIG. 1. Application 81 generates a model of a region of interest containing the target based on images of the region of interest and identifies the target within the model of the region of interest. Using the drawings, application 81 further predicts a path by which access instrument 200 may be guided to reach the target. Application 81 recognizes solid items, such as bones, and essential organs that may not safely be punctured in the images and determines an insertion point and angle to allow access instrument 200 to be guided in a straight line to the target. As the access instrument 200 advances through the patient toward the target, application 81 tracks the location of EM sensor 94 while EM sensor 94 is advanced within of a region of interest.

Access instrument 200 is a luminal device that may puncture the patient's skin, and if necessary other tissue and organs, in order to be guided toward a target, such as a tumor or other malady. Access instrument 200 may be, for example, a trocar or a needle. Access instrument 200 is configured to receive a tool 120. Access instrument 200 is guided, as described above, through the skin and other tissue. Once access instrument 200 is guided proximate the target, tool 120 is inserted into access instrument 200. As tool 120 advances toward the target, indicator 122 moves proximate EM sensor 94. When indicator 122 is proximate EM sensor 94, EM sensor 94 senses a change in the magnetic field caused by indicator 122 and determines that indicator 122 is proximate. Accordingly, application 81 may then update the progression of the tool according to a known location of indicator 122 along tool 120. The progression of the tool is used to update a distance between the tool and the target and may be used to update the model of the region of interest to include a location of the approaching tool. The updated display may then be displayed on monitoring equipment 60.

Figure 3:
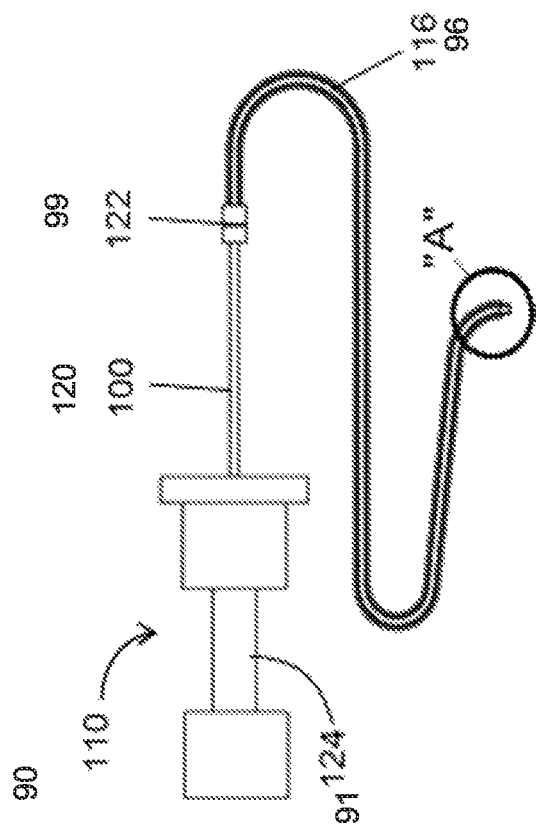
FIG. 3 is a perspective view of a catheter guide assembly of the EMN system of FIG. 1, in accordance with the present disclosure.

With reference to FIG. 3, a catheter guide assembly 90 is shown, in accordance with an embodiment of the present disclosure. In addition to including EWC 96 and tool 120, the catheter guide assembly 90 includes a control handle 91, which enables advancement and steering of the distal end of the catheter guide assembly 90. Once inserted in EWC 96, tool 120 can be locked to EWC 96 with a locking mechanism 99. The locking of tool 120 to EWC 96 allows tool 120 and EWC 96 to travel together through a luminal network of the patient "P." Locking mechanism 99 may be a simple clip or luer lock, or the tool 120 may have a threaded configuration that allows it to threadably engage with and lock to the EWC 96. Examples of catheter guide assemblies usable with the instant disclosure are currently marketed and sold by Medtronic plc under the name SUPERDIMENSION® Procedure Kits and EDGE™ Procedure Kits. For a more detailed description of the catheter guide assemblies, reference is made to commonly-owned U.S. Pat. Nos. 9,247,992 and 7,233,820, the entire contents of which are incorporated in this disclosure by reference.

In some embodiments of the present disclosure, tool 120 is inserted into EWC 96 and locked into place proximate a distal tip of EWC 96 via a locked mechanism (not explicitly shown). Tool 120 may be locked into place flush with the distal tip of EWC 96 or tool 120 may be locked into place extending beyond the distal tip of EWC 96 at a known distance. Once tool 120 is locked within EWC 96, tool 120 and EWC 96 may be advanced toward the target together. If tool 120 must be moved independent or incrementally of EWC 96, tool 120 may be unlocked from EWC 96 and advanced independently. Upon reaching an intended position with respect to EWC 96, tool 120 may then be locked into EWC 96. Thus, if EM sensor 96 is coupled to EWC 96 at a known point and tool 120 extends beyond EWC 96 a known distance, application 81 may determine a location of the tool 120 when EM sensor 94 recognizes indicator 122. Moreover, once application 81 determines the location of tool 120, application 81 further determines a distance between tool 120 and the target. Accordingly, as tool 120 approaches the target, a trajectory of tool 120 may be updated in order to aid the clinician in navigating tool 120 to the target.

Figure 4C:
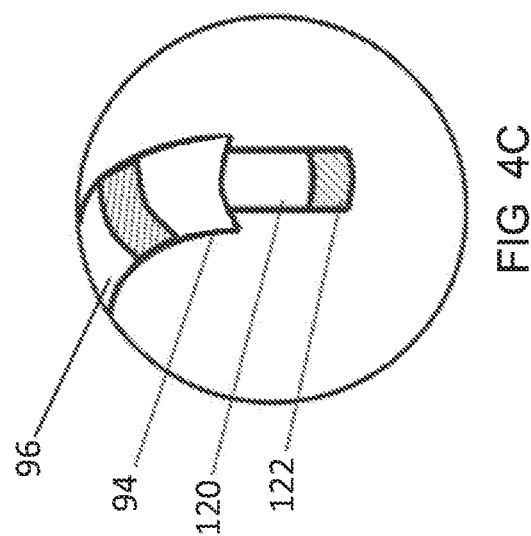
FIG. 4C is an enlarged view of an alternative embodiment of the distal portion of the catheter guide assembly of FIG. 3 indicated by area "A"
Figure 4B:
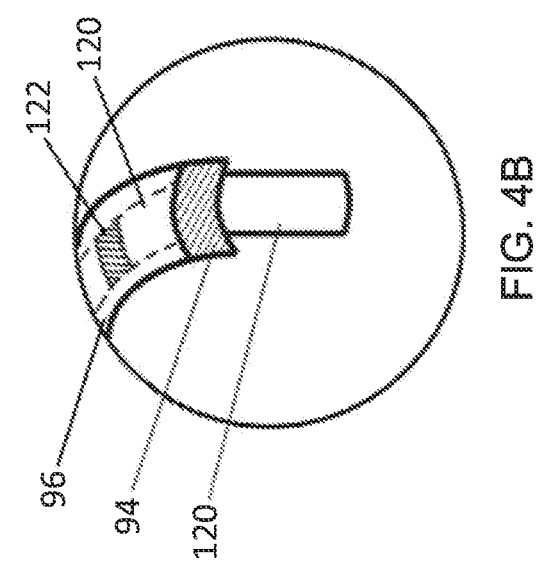
FIG. 4B is an enlarged view of an alternative embodiment of the distal portion of the catheter guide assembly of FIG. 3 indicated by area "A"
Figure 4A:
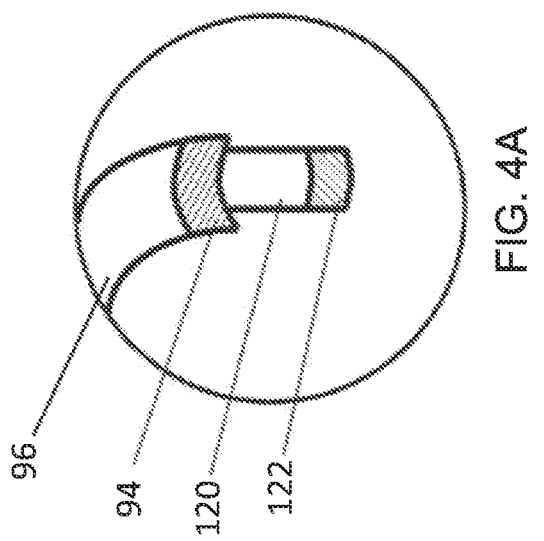
FIG. 4A is an enlarged view of an embodiment of a distal portion of the catheter guide assembly of FIG. 3 indicated by area "A"

FIGS. 4A-C are enlarged views of a distal portion of catheter guide assembly 90 indicated by an encircled area "A" in FIG. 3. Here, the EWC 96 including an EM sensor 94 is shown with tool 120 protruding therefrom. In FIG. 4A, EM sensor 94 is shown located at the distal-most portion of EWC 96 and indicator 122 is shown located at the distal-most portion of tool 120. The configuration of FIG. 4A allows for a distance between the distal tip of EWC 96 and the distal tip of tool 120 to be determined. In FIG. 4B, EM sensor 94 remains positioned at the distal-most portion of EWC 96, but indicator 122 is shown located a distance from the distal-most portion of tool 120. The distance between the distal-most portion of tool 120 and indicator 122 may be a known distance that can establish a location of the distal-most portion of tool 120 outside of EWC 96. The distance between the distal-most portion of tool 120 and indicator 122 may be pre-determined and manufactured into the tool, or the location of indicator 122 may be moveable to, for instance, a distance equal to the distance between a wedging location of EWC 96 and the target. There may additionally be several indicators 122 located at several locations along the length of tool 120 to generate multiple location points by which to update a location of tool 120. In FIG. 4C, indicator 122 is shown located at the distal-most portion of tool 120, and EM sensor 94 is shown located at a distance from the distal-most portion of EWC 96. Similar to the repositioning of indicator 122, EM sensor 94 may be positioned at a distance from the distal-most portion of EWC 96. The location of EM sensor 94 may be static, built-in, or moveable.

In FIGS. 4A-C, tool 120 is shown within, and protruding from, EWC 96. However, the configurations shown in FIGS. 4A-C are also usable utilizing access instrument 200 in place of EWC 96. Tool 120 travels through access instrument 200 and protrudes from the distal end of access instrument 200. EM sensor 94 may be located at various locations along the length of access instrument 200, and indicator 122 may be located at various locations along tool 120 to enable a clinician to choose the most ideal combination for monitoring the movement of tool 120 as it approaches the target.

Though FIGS. 4A-C show EM sensor 94 at or near a distal-most end of EWC 96. EM sensor 94 or an alternative sensor may be placed anywhere along EWC 96 or bronchoscope 50, including proximal portions of EWC 96 and bronchoscope 50. No matter where along the length of EWC 96 or bronchoscope 50 the sensor is located, a known location or a known distance between the location of the sensor and the end of EWC 96 or bronchoscope 50 allows a distance between the distal portion of EWC 96 or bronchoscope 50 and tool 120 to be known.

Indicators 122 are described above as elements applied to tool 120. However, it is also contemplated in the present disclosure that tool 120 will possess innate electromagnetic characteristics detectable by EM sensor 94. While those characteristics may vary from tool 120 to tool 120, a library of tools may be generated based on electromagnetic characteristics of specific tools 120 from specific manufacturers. Once a library is developed, the electromagnetic characteristics of tool 120 may operate as indicators 122. The electromagnetic characteristics vary depending on a location along tool 120 such that EM sensor 94 senses a distortion in the electromagnetic field, and application 81 receives the sensed distortion and compares it to library readings for the given tool 120 type and model to determine a location of tool 120 relative to EM sensor 94. The type and model of the tool may be input by a clinician or read via a barcode, RFID, or any other suitable indicator capable of containing information regarding tool 120.

Turning now to FIG. 5, there is shown a distal portion of EWC 96, including EM sensor 94, with tool 120, including indicator 122, protruding from therefrom and approaching target "T." Upon reaching the location of EM sensor 94, the location of tool 120 with respect to indicator 122 is established at a distance D2 from target "T." As the distal portion of tool 120 exits EWC 96, a distance D1 may be tracked by application 81. Once, according to application 81, D1 is equal to D2, location of tool 120 will be presumed or estimated to be within the target and treatment may commence. In the alternative, indicator 122 may be located a distance from the distal-most portion of tool 120. In this scenario, a distance D1 could represent a known distance between indicator 122 and the distal-most portion of tool 120. Accordingly, an approach distance is established by subtracting D1 from D2. The determined approach distance may then be used to update the model or update a location of the tool according to the model.

FIG. 5 shows tool 120 protruding through EWC 96. As an alternative, EWC 96 need not be used. EM sensor 94 may instead be located on bronchoscope 50, and distance D1 may indicate a distance between a distal portion of bronchoscope 50 and a distal portion of tool 120.

As a further alternative, EWC 96 includes indicator 122 and bronchoscope 50 includes EM sensor 94. EWC 96 is configured to travel through, and protrude from, bronchoscope 50. Then, a distance D1 may be determined between a distal portion of bronchoscope 50 and a distal portion of EWC 96.

Figure 6:
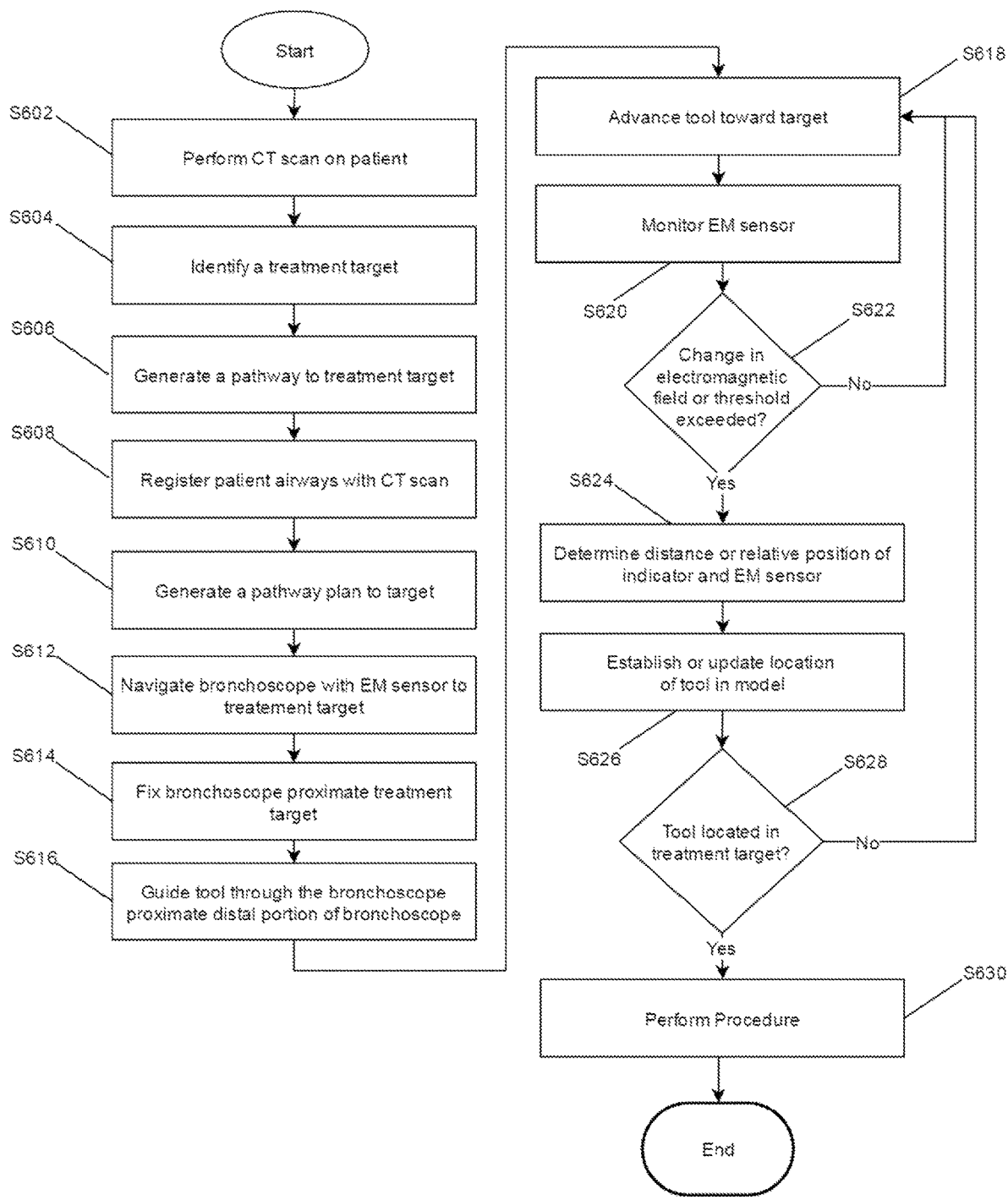
FIG. 6 is a flow diagram of a method for navigating a catheter and a tool to a target site, in accordance with an embodiment of the present disclosure.
Figure 7:
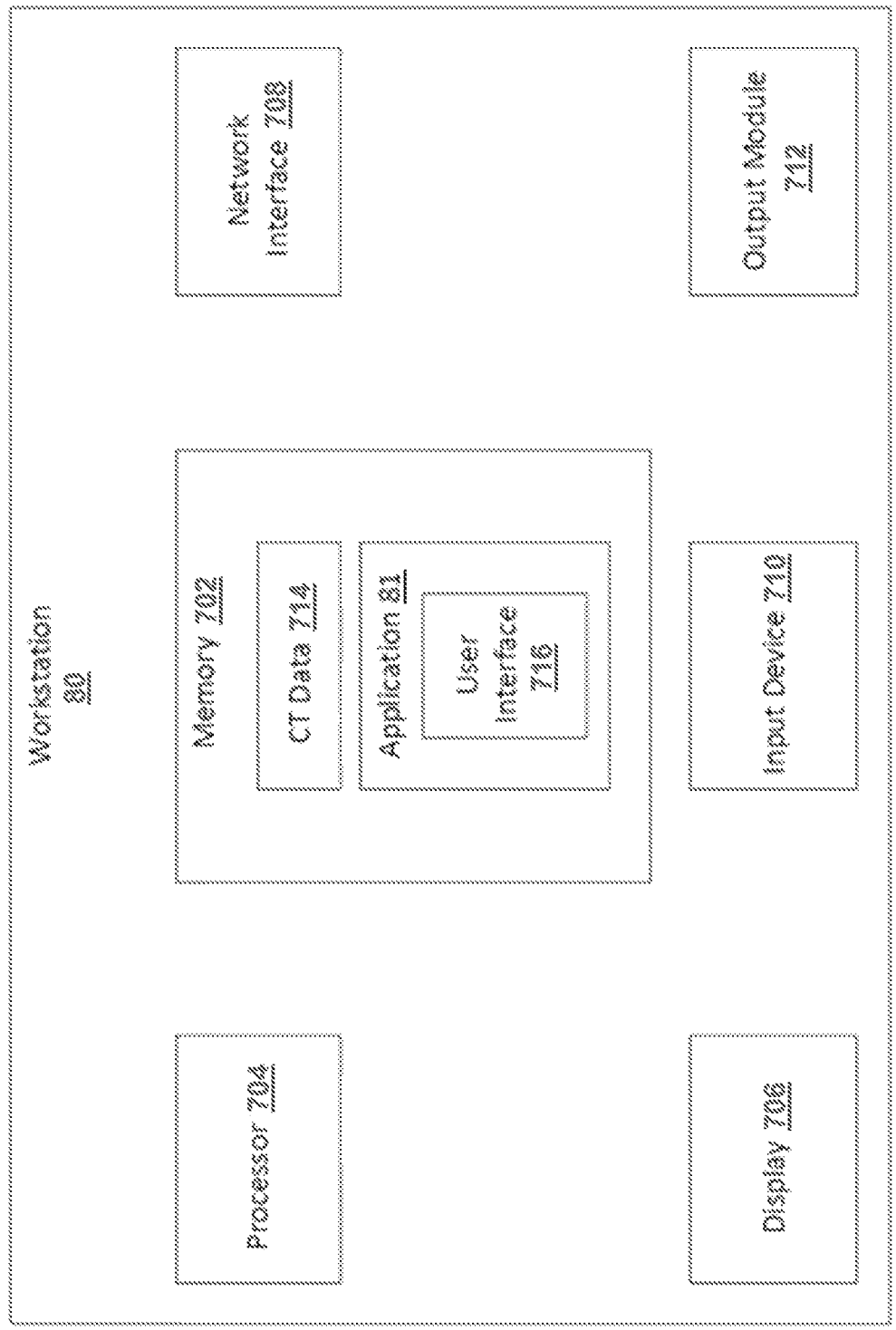
FIG. 7 is a schematic of the components of a workstation that may be implemented in the EMN system of FIG. 1, in accordance with an embodiment of the present disclosure.

With reference now to FIG. 6, there is shown a flowchart of a process for navigating to target "T" and tracking the distance between tool 120 and target site "T." The process may be implemented, at least in part, by workstation 80 and by application 81. In performing the process, processor 704 executes instructions stored in the memory 702 (FIG. 7). The particular sequence of steps shown in FIG. 6 may be executed in sequences other than the sequence shown in FIG. 6 without departing from the scope of the present disclosure. Further, some steps shown in process of FIG. 6 may be concurrently executed with respect to one another instead of sequentially executed with respect to one another. The process of FIG. 6 is described with reference to FIGS. 1-5.

The process begins at step S602. At step S602, an area of interest, for instance the chest and lungs, of a patient is imaged using imaging methods such as, for example, a CT scan. At step S604, a target is identified in the images generated in step S602. Once a target is established, at step S606, a path through the branches of the airways (in some instances identifying the registration points along the path and near the target) is generated in the CT image data.

In the alternative, if a percutaneous procedure is being performed, application 81 may generate a path to the target directly through the patient's skin. For a percutaneous procedure, registration points may be established outside of the patient's body, as well as inside the body that along the path established for the approach of access instrument 200 to the target. The path for a percutaneous procedure includes, at least, an insertion location, an insertion angle, and a depth of insertion trackable via the same or similar means as described above.

Once the pathway plan has been developed and is accepted by the clinician, the pathway plan can be utilized in a navigation procedure using the EMN system 70 or access instrument 200. The pathway plan is loaded into application 81 on workstation 80 and displayed.

Then, at step S608, application 81 performs the registration of the CT scan with the patient's airways, as described above, and in particular as described in co-pending U.S. Patent Publication No. 2016-0000356, entitled REAL TIME AUTOMATIC REGISTRATION FEEDBACK, filed on Jul. 2, 2015, by Brown et al., the entire contents of which are incorporated herein by reference. During registration, the location of EM sensor 94 within the patient's airways is tracked, and a plurality of points denoting the location of EM sensor 94 within the EM field generated by EM generator 76 is generated. When sufficient points have been collected, the application 81 compares the locations of these points to the 3D model and seeks to fit all the points within the lumens of the 3D model. When a fit is established, signifying that the majority if not all of the points have been fit within the area defined by the 3D model of the airway, the patient and the 3D model are registered to one another. As a result, detected movement of the EM sensor 94 within the patient can be accurately depicted on the display of the workstation 80 as a sensor 94 traversing the 3D model or a 2D image from which the 3D model was generated.

After the pathway plan has been developed and is accepted by the clinician, the pathway plan can be utilized in a navigation procedure using the EMN system 10. Application 81 begins navigation process, at step S612 by displaying guidance for navigating EM sensor 94 to the target while tracking the location of EM sensor 94. In the alternative, by viewing a live video feed from a camera located proximate EM sensor 94 (e.g., in a bronchoscope) a target may be detected visually by a clinician. Once bronchoscope 50 and/or EWC 96 are navigated to a target treatment site, at step S614, catheter 115 is guided through bronchoscope 50 or EWC 96 to the target.

If a percutaneous procedure is being performed, after the pathway plan has been developed and is accepted by the clinician, the pathway plan can be utilized in navigating access instrument 200 to the target. Application 81 begins navigation process, at step S612 by displaying guidance for navigating EM sensor 94 to the target while tracking the location of EM sensor 94.

At step S614, bronchoscope 50, EWC 96, or access instrument 200 is fixed into place proximate the target. Locking or stabilizing bronchoscope 50, EWC 96, or access instrument 200 ensures that EM sensor 94 senses minimal fluctuations in the electromagnetic field due to movement of EM sensor 94 within the electromagnet field. Once fluctuations in the electromagnet field due to movement of EM sensor 94 are minimized, fluctuations in the field may more confidently be determined to indicate the proximity of indicator 122 to EM sensor 94. Bronchoscope 50 or EWC 96 may be locked in place by wedging bronchoscope 50 into, for example, a luminal passage, by expanding a catheter balloon (not shown), by positioning and engaging an endobronchial valve, or through several additional means commonly known in the art. Access instrument 200 generally will stabilize merely through the process of guiding access instrument 200 through various layers of tissue. Nonetheless, additional elements, such as ribbing or crenelated portions along access instrument 200, may aid in stabilizing access instrument 200.

At step S616, a clinician guides tool 120 through bronchoscope 50, EWC 96, or access instrument 200. A clinician or a robotic arm may push tool 120 through access instrument 200, bronchoscope 50, or EWC 96 to a distal portion of access instrument 200, bronchoscope 50, or EWC 96 proximate EM sensor 94. Control handles 91 may also be used to guide tool 120 and/or EWC 96 through bronchoscope 50.

Once tool 120 is proximate EM sensor 94, a clinician, at step S618, may further advance tool 120 toward the target. As tool 120 approaches the target, indicator 122 similarly approaches EM sensor 94. As indicator 122 approaches EM sensor 94, the ferromagnetic properties of indicator 122 causes the electromagnetic field measured by EM sensor 94 to fluctuate and change. Application 81, at step S6202, receives and monitors readings from EM sensor 94 while the electromagnetic field fluctuates and changes as a result of indicator 122 approaching, and determines that (because bronchoscope 50, EWC 96, or access instrument 200, and therefore EM sensor 94 which is located on one of the bronchoscope 50, EWC 96, or access instrument 200, is stabilized or locked into position within the area of interest), indicator 122 is approaching. If, at step S622, a change in the electromagnetic field is detected by EM sensor 94, the process proceeds to step S624. Alternatively, if a measurement of the electromagnetic field, by EM sensor 94, exceeds a certain threshold the process proceeds to step S624. If no change in the electromagnetic field is detected or if the magnitude of the measurement of the electromagnetic field does not exceed a threshold, the process returns to steps S618 through S620 until a change in the electromagnetic field is detected or until the magnitude of the detected electromagnetic field exceeds the threshold. For other types of indicators 122 and sensors, other than EM sensor 94, changes in other measurable qualities may also be detected including, but not limited to, color, physical dimensions (including thickness, length, surface roughness, etc.), magnetic properties, and capacitance.

At step S624, application 81 determines a distance or relative position between indicator 122 and EM sensor 94. The strength of the fluctuations in the electromagnetic field increases as indicator 122 approaches EM sensor 94, reaches a peak when indicator 122 is at the closest possible position to EM sensor 94, and subsequently decreases as indicator 122 proceeds distal away from EM sensor 94. Application 81 may therefore determine a distance between EM sensor 94 and indicator 122 based on the fluctuations or changes in the electromagnetic field or based on the magnitude of the electromagnetic field. If application 81 determines that the magnitude of the electromagnetic field exceeds a threshold value, application 81 determines that indicator 122 is positioned at or within a limited distance of EM sensor 94. Once application 81 determines indicator 122 is positioned at or within a limited distance of EM sensor 94, application 81 may count down the distance between a distal portion of tool 120 and the target, as further explained in step S626

At step S626, the distance or relative position between indicator 122 and EM sensor 94 is used to update or establish a location of tool 120 in the model of the region of interest containing the target. As EM sensor 94 travels through the electromagnetic field, application 81 determines a location of EM sensor 94 and displays the location of EM sensor 94 in the model of the region of interest on monitoring equipment 60. Accordingly, a location of the item to which EM sensor 94 is coupled (e.g., bronchoscope 50, EWC 96, access instrument 200 or another device), can be shown within the model. Once a distance or a position of indicator 122 is known in relation to EM sensor 94, a position of tool 120, to which indicator 122 is coupled, within the of the region of interest on monitoring equipment is determined and displayed on monitoring equipment 60 to guide the clinician's approach to the target. Upon establishing a position of tool 120 in the model of the region of interest, application 81 may determine the relative distance between tool 120 and the target on the model in order to count down the distance between the distal portion of tool 120 and the target.

A location of the tool may be otherwise known using sensors and therefore a relative position of tool 120 determined by measuring fluctuations in the magnetic field caused by indicator 122 may be used to update a location of tool 120.

At step S628, the clinician performing the procedure, by observing a status of tool 120 on monitoring equipment 60, or application 81, using the distance countdown within the model, determines whether the distal portion of tool 120 is located in the target for performing a procedure. If the tool is not located at the target, such that the procedure can be performed, the process returns to step S618 and repeats steps S618 through S626 to monitor the approach of tool 120 to the target until the distal portion of tool 120 is confirmed to be located in the target. When the distal portion of tool 120 is positioned within the treatment, the process proceeds to step S630, in which a procedure, such an ablation or a biopsy procedure, is performed.

Turning now to FIG. 7, there is shown a system diagram of workstation 80. Workstation 80 may include memory 702, processor 704, display 706, network interface 708, input device 710, and/or output module 712.

Memory 702 includes any non-transitory computer-readable storage media for storing data and/or software that is executable by processor 704 and which controls the operation of workstation 80. In an embodiment, memory 702 may include one or more solid-state storage devices such as flash memory chips. Alternatively or in addition to the one or more solid-state storage devices, memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media includes non-transitory, volatile and non-volatile, removable and non-removable media implemented in any method or technology for storage of information such as computer-readable instructions, data structures, program modules or other data. For example, computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 702 may store application 81 and/or CT data 214. Application 81 may, when executed by processor 704, cause display 706 to present user interface 716. Network interface 708 may be configured to connect to a network such as a local area network (LAN) consisting of a wired network and/or a wireless network, a wide area network (WAN), a wireless mobile network, a Bluetooth network, and/or the internet. Input device 710 may be any device by means of which a clinician may interact with workstation 80, such as, for example, a mouse, keyboard, foot pedal, touch screen, and/or voice interface. Output module 712 may include any connectivity port or bus, such as, for example, parallel ports, serial ports, universal serial busses (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

Detailed embodiments of such devices, systems incorporating such devices, and methods using the same are described above. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the example embodiments described above are directed to the bronchoscopy of a patient's airways, those skilled in the art will realize that the same or similar devices, systems, and methods may also be used in other lumen networks, such as, for example, the vascular, lymphatic, and/or gastrointestinal networks. Those skilled in the art would also recognize that the same or similar devices, systems, and methods may also be used to perform a percutaneous procedure or in procedures in which a device is navigated through a luminal network before puncturing through a wall in the luminal network to reach a target.

Though written generally as applying to bronchoscopic and percutaneous approaches for treatment and diagnostic procedures, those of skill in the art will readily recognize that these same or similar techniques, systems and methods may be employed for laparoscopic approaches (e.g., using one or more transdermal ports and a laparoscopic camera) or other endoscopic approaches when accessing other portions of the body including but not limited to the large and small intestine, the vascular networks, cardiac spaces, and the like.

What is claimed is:

1. A system for monitoring an approach to a target, the system comprising:
    a luminal device including a distal end and configured to be inserted into a patient, the distal end of the luminal device configured to be guided proximate the target and including a sensor;
    a surgical instrument configured to be guided through the luminal device, the surgical instrument including one or more indicators having a detectable property located along at least a portion of the surgical instrument; and
    a computing device operably coupled to the sensor and including a processor and a memory storing instructions which, when executed by the processor, cause the computing device to:
        receive a signal from the sensor corresponding to a magnitude of distortion in an electromagnetic field;
        convert the signal to a distance between the sensor and the one or more indicators; and
        calculate a location of the one or more indicators based on the distance between the sensor and the one or more indicators.

2. The system of claim 1, wherein the sensor is configured to sense the detectable property of the one or more indicators for determining a distance that the surgical instrument has advanced beyond the sensor.

3. The system of claim 1, further comprising:
    an electromagnetic field generator configured to generate the electromagnetic field; and
    a display capable of displaying an image of the sensor within the patient,
    wherein the instructions, when executed by the processor, cause the computing device to:
        generate a model of a region of interest containing the target based on images of the region of interest;
        identify the target within the model of the region of interest; and
        track the location of the sensor while the sensor is navigated within the region of interest.

4. The system of claim 3, wherein the region of interest is a luminal network.

5. The system of claim 1, wherein the detectable property is ferromagnetism.

6. The system of claim 1, further comprising an electromagnetic field generator configured generate an electromagnetic field, wherein the sensor is an electromagnetic sensor capable of detecting a change in the electromagnetic field caused by the one or more indicators.

7. The system of claim 1, wherein the one or more indicators are stripes or flecks.

8. The system of claim 1, wherein the luminal device is one of a catheter, a needle, or a trocar.

9. The system of claim 1, wherein the one or more indicators are painted on or implanted within the surgical instrument.

10. The system of claim 1, wherein the one or more indicators includes a plurality of indicators, each indicator of the plurality of indicators being located at even intervals along a length of the surgical instrument.

11. The system of claim 1, wherein the one or more indicators includes a plurality of indicators each having a distinct known material composition or concentration of charged particles that defines each of the one or more indicators or defines a progression of the one or more indicators.

12. The system of claim 1, further comprising:
    a second sensor coupled to the luminal device at a different location than a location of the sensor, the second sensor configured to sense the detectable property of the one or more indicators.

13. The system of claim 1, wherein the sensor defines a lumen and the surgical instrument is configured to be guided through the lumen of the sensor.

14. The system of claim 1, wherein the luminal device defines a lumen and the surgical instrument is configured to extend through the lumen of the luminal device.

15. A system for monitoring an approach to a target, the system comprising:

a luminal device including a distal end and configured to be inserted into a patient, the distal end of the luminal device configured to be guided proximate the target and including a sensor defining a lumen;

a surgical instrument configured to be guided through the luminal device and the lumen of the sensor, the surgical instrument including one or more indicators having a detectable property located along at least a portion of the surgical instrument; and a computing device operably coupled to the sensor and including a processor and a memory storing instructions which, when executed by the processor, cause the computing device to:

determine a distance between the sensor and the one or more indicators; and calculate a location of the one or more indicators based on the distance between the sensor and the one or more indicators.

16. The system of claim 15, further comprising an electromagnetic field generator configured generate an electromagnetic field, wherein the sensor is an electromagnetic sensor capable of detecting a change in the electromagnetic field caused by the one or more indicators.

17. The system of claim 15, wherein the luminal device is one of a catheter, a needle, or a trocar.

18. A system for monitoring an approach to a target, the system comprising:

a luminal device including a distal end and configured to be inserted into a patient, the distal end of the luminal device configured to be guided proximate the target and including a first sensor and a second sensor;

a surgical instrument configured to be guided through the luminal device, the surgical instrument including one or more indicators having a detectable property located along at least a portion of the surgical instrument, wherein the second sensor is configured to sense the detectable property of the one or more indicators; and a computing device including a processor and a memory storing instructions which, when executed by the processor, cause the computing device to:

determine a distance between the first sensor and the one or more indicators; and calculate a location of the one or more indicators based on the distance between the first sensor and the one or more indicators.

19. The system of claim 18, further comprising an electromagnetic field generator configured generate an electromagnetic field, wherein the first sensor is an electromagnetic sensor capable of detecting a change in the electromagnetic field caused by the one or more indicators.

20. The system of claim 18, wherein at least one of the first sensor or the second sensor defines a lumen and the surgical instrument is configured to extend through the lumen.

* * * * *